United States Patent
Borgman et al.

(10) Patent No.: US 6,913,759 B2
(45) Date of Patent: Jul. 5, 2005

(54) GEL COMPOSITION AND METHOD FOR TREATMENT OF VAGINAL INFECTIONS

(75) Inventors: Robert J. Borgman, Mundelein, IL (US); James E. Juul, Wauconda, IL (US)

(73) Assignee: Curatek Pharmaceuticals Holding, Inc., Elk Grove Village, IL (US)

( * ) Notice: Subject to any disclaimer, the term of this patent is extended or adjusted under 35 U.S.C. 154(b) by 63 days.

(21) Appl. No.: 10/386,281

(22) Filed: Mar. 11, 2003

(65) Prior Publication Data

US 2004/0180965 A1 Sep. 16, 2004

(51) Int. Cl.[7] .................... A61K 31/416; A61K 31/415; A61K 9/00; A61K 9/10; A01N 25/04
(52) U.S. Cl. .................... 424/405; 424/400; 424/407; 424/484; 424/486; 514/405
(58) Field of Search ................ 424/400, 405, 424/407, 484, 480; 514/405

(56) References Cited

U.S. PATENT DOCUMENTS 5,840,744 A * 11/1998 Borgman .................... 514/398

FOREIGN PATENT DOCUMENTS

WO     WO 96/26724    *   9/1996  ......... A61K/31/44

* cited by examiner

Primary Examiner—Thurman K. Page
Assistant Examiner—Simon J. Oh
(74) Attorney, Agent, or Firm—Olson & Hierl, Ltd.

(57) ABSTRACT

A pharmaceutical composition having a gel consistency at room temperature and suitable for the treatment of a vaginal infection comprises, on a total composition weight basis, about 0.1 to about 3 weight percent of benzydamine hydrochloride, about 16 to about 35 weight percent of a polyoxyalkylene block copolymer, and about 2 to about 30 weight percent of propylene glycol, in water having a pH value in the range of about 3.5 to about 7. The weight ratio of water to polyoxyalkylene block copolymer in the composition is less than about 4:1. Optionally, the gel compositions can also contain glycerin, physiologically tolerable preservatives and buffers, as well as other pharmaceutically acceptable excipients.

21 Claims, No Drawings

GEL COMPOSITION AND METHOD FOR TREATMENT OF VAGINAL INFECTIONS

FIELD OF THE INVENTION

The invention relates generally to compositions and treatments for vaginal infections. More particularly, the invention relates to gel compositions suitable for treatment of vaginal infections comprising a polyoxyalkylene block copolymer gelling agent and benzydamine.

BACKGROUND OF THE INVENTION

Bacterial vaginosis (BV) is associated with an increased volume of vaginal discharge having a foul, fishy odor. Vaginal pH is elevated from the normal range (pH 3–4) to values greater than or equal to about pH 4.7. The odor and elevated pH are caused by a high level of amines, most notably trimethylamine, in the vagina. These amines are volatilized when the pH is raised, for example, as with addition of KOH or interaction with semen. The vaginal discharge is homogenous in appearance as opposed to the flocculent discharge seen in candidiasis. In contrast to candidiasis and trichomoniasis, itching generally is not associated with BV. A microscopic examination of a wet mount of the vaginal discharge in BV reveals an absence of polymorphonuclear leukocytes (PMNs). In contrast, the presence of many PMNs in a vaginal discharge is indicative of trichomoniasis, gonorrhea, or chlamydial cervicitis.

Typically, a clinical diagnosis of BV is made if three or more of the following four clinical criteria are present: (1) a homogenous discharge; (2) a pH value greater than or equal to about 4.7; (3) a "fishy" amine odor upon the addition of 10% KOH to discharge; (4) presence of epithelial clue cells in an amount greater than or equal to about 20% of vaginal epithelial cells.

Vulvovaginal candidiasis is a relatively common form of yeast infection involving an over-proliferation of *Candida albicans* and related species in the vulvovaginal region. The disease can be treated with anti-fungal compositions such as miconazole nitrate. One common regimen for treating vulvovaginal candidiasis with miconazole nitrate comprises repeated intra-vaginal application of a cream containing miconazole nitrate over a period of several days to about a week.

U.S. Pat. No. 5,536,743 to Borgman describes a pH buffered, aqueous gel formulation of the antimicrobial agent metronidazole for treatment of BV. While providing an effective treatment for BV, metronidazole gel has been reported to have some undesirable side effects in some patients, such as yeast vaginitis following therapy, vulvovaginal irritation, and gastrointestinal discomfort. In addition, metronidazole can have adverse interactions with alcohol ingested by the patient.

Benzydamine hydrochloride (B—HCl) is a non-steroidal anti-inflammatory drug (NSAID) that is commercially available in Europe and other countries for topical application. B—HCl has the dual advantage of being an analgesic as well as having anti-microbial activity. A cream formulation of B—HCl, available under the trade name TANTUM ROSA® from Angelini Pharmaceuticals, Rome, Italy, has been utilized in a number of countries as a topical treatment for vaginal infections. The cream formulation, however, has a disadvantage of being difficult to administer intravaginally, remains in contact with the vaginal tissue for a relatively short period of time, and provides relatively rapid delivery of the active agent (B—HCl). These factors lead to a necessity for multiple applications of the cream formulation over a six to ten day period in order to treat a vaginal infection.

A desirable treatment for vaginal infections would be a sustained-release gel composition for intravaginal administration that delivers the active agent over an extended period of time and remains in contact with the vaginal tissue for a time period sufficient for substantially all of the active agent to be released. The present invention provides such a desirable treatment in the form of an aqueous polyoxyalkylene block copolymer gel formulation of B—HCl.

SUMMARY OF THE INVENTION

A pharmaceutical gel composition useful for treating vaginal infections comprises, on a total composition weight basis, about 0.1 to about 3 weight percent of benzydamine hydrochloride, about 16 to about 35 weight percent of a polyoxyalkylene block copolymer, and about 2 to about 50 weight percent of propylene glycol, in water having a pH in the range of about 3.5 to about 7. The weight ratio of water to polyoxyalkylene block copolymer in the composition preferably is less than about 4:1, more preferably not more than about 3:1. In one preferred embodiment the composition also includes glycerin. In other preferred embodiments the composition can include physiologically tolerable preservatives, such as parabens and chelating agents, and/or electrolyte salts such as sodium chloride.

The sustained-release gel compositions of the present invention provide a release of the active agent (benzydamine hydrochloride) over an extended period of time, and can remain in contact with vaginal tissue for a time period sufficient to release substantially all of the active agent. The gel compositions of the present invention are particularly well suited for the treatment of bacterial and yeast infections of the vagina.

A method aspect of the present invention involves contacting the vagina of a human or veterinary patient suffering from a vaginal infection with a therapeutically effective amount of a gelled pharmaceutical composition of the present invention.

DETAILED DESCRIPTION OF PREFERRED EMBODIMENTS

As used herein and in the appended claims, the term "polyoxyalkylene block copolymer" and grammatical variations thereof, refer to copolymers of alkylene oxides such as ethylene oxide and propylene oxide, which form a gel when dispersed in water in sufficient concentration. Preferred polyoxyalkylene block copolymers include polyoxyethylene/polyoxypropylene block copolymers (EO/PO block copolymers) commonly referred to as poloxamer polymers, and which have the general formula (I):

$$HO(CH_2CH_2O)_x(CH(CH_3)CH_2O)_y(CH_2CH_2O)_zH, \quad (I)$$

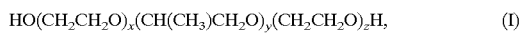

according to the *International Cosmetic Ingredient Dictionary and Handbook*, Volumes 1–3, Seventh Edition, (1997) published by the Cosmetic, Toiletry, and Fragrance Association, Washington D.C. Preferably, x, y, and z are each integers in the range of about 10 to about 150, representing the average number of monomer units in the polymer; the values of x and z are frequently substantially equal to each other. Examples of poloxamer polymers suitable for use in the gelled pharmaceutical compositions of the present invention are EO/PO block copolymers commercially available under the trade name PLURONIC® from BASF Corporation, Mount Olive, N.J. A preferred poloxamer polymer is PLURONIC® F127 (also known as poloxamer 407), which has the formula (I) with average values of x and z in the range of about 98 to about 101, and y in the range of about 56 to about 67, respectively.

As used herein and in the appended claims the term "gel" in reference to the present aqueous pharmaceutical compositions, means that the composition is relatively non-flowing at ambient temperature (about 25° C.).

The terms "pharmaceutically acceptable", "physiologically tolerable", "physiologically compatible", and grammatical variations thereof, as used herein and in the appended claims as they refer to electrolytes (e.g., salts), bases, diluents, preservatives, buffers and other excipients, are used interchangeably and represent that the materials are capable of topical administration to human skin and to the human vagina without the production of undesirable physiological effects such as irritation, itching, stinging, or systemic effects such as nausea, dizziness, and the like.

The terms "vagina" and "vulvovaginal" as used herein and in the appended claims encompasses the vaginal region generally, including also the vulva and the cervix, of a human or veterinary patient.

The term "therapeutically effective amount" as used herein and in the appended claims, in reference to pharmaceutical compositions, means an amount of pharmaceutical composition that will elicit the biological or medical response of a patient that is sought by a clinician.

A gelled pharmaceutical composition of the present invention is an aqueous gel comprising benzydamine hydrochloride as the active anti-microbial agent. The chemical structure of benzydamine hydrochloride is shown in formula (II).

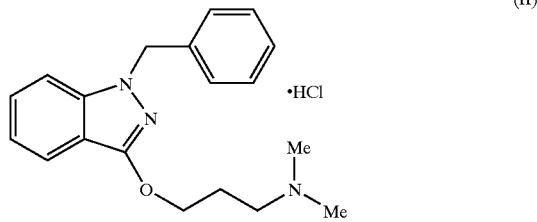

(II)

Benzydamine hydrochloride (B—HCl) is a non-steroidal antiinflammatory drug (NSAID) that also has anti-bacterial activity against both Gram-positive and Gram-negative bacteria, as well as anti-fungal activity. The compositions of the present invention preferably include about 0.1 to about 3 weight percent of B—HCl, more preferably about 0.75 to about 2 weight percent, on a total composition weight basis. Benzydamine hydrochloride is a commercially available compound.

The gel compositions of the present invention also include a polyoxyalkylene block copolymer, such as a poloxamer polymer, as a gelling agent and carrier for the active antimicrobial agent. The polyoxyalkylene block copolymer is present in the composition preferably in an amount in the range of about 16 to about 35 weight percent, more preferably about 20 to about 30 weight percent, on a total composition weight basis.

The compositions of the present invention also include propylene glycol, in an amount in the range of about 2 to about 50 weight percent, preferably about 3 to about 30 weight percent, on a total composition weight basis.

The compositions of the present invention optionally can include a physiologically tolerable preservative, a buffer system, as well as pharmaceutically acceptable excipients, so long as the optional components do not interfere with the gelling of the composition or with the release of the benzydamine hydrochloride in the vagina.

Suitable physiologically tolerable preservatives include bacteriostats, preservatives, inhibitors, and the like, such as methyl, ethyl, propyl, and butyl esters of parahydroxybenzoic acid (paraben); propyl gallate; sorbic acid and its sodium and potassium salts; propionic acid and its calcium and sodium salts; 6-acetoxy-2,4-dimethyl-m-dioxane; 2-bromo-2-nitropropane-1,3-diol; salicylanilides such as dibromosalicylanilide and tribromosalicylamilide, the cis isomer of 1-(3-chloroallyl-3,5,7-triaza-1-azanidadamantane chloride; hexachlorophene; sodium benzoate; chelating agents such as ethylene diaminetetraacetic acid (EDTA), citric acid, and their alkali metal salts; phenolic compounds such as butyl hydroxyanisol, butyl hydroxytoluene, chloro- and bromo-cresols, and chloro- and bromo-oxylenols; quaternary ammonium compounds such as benzalkonium chloride; aromatic alcohols such as 2-phenylethyl alcohol and benzyl alcohol; chlorobutanol; quinoline derivatives such as iodochlorohydroxyquinoline; and the like.

Preferred physiologically tolerable preservatives include parabens (e.g., methyl paraben, propyl paraben, mixtures thereof, and the like), chelating agents (e.g, EDTA or a physiologically tolerable salt thereof, such as sodium edatate, disodium edatate, and the like), and mixtures thereof. Preferably, the preservative is included in an amount in the range of about 0.05 to about 0.2 weight percent, on a total composition weight basis.

Suitable buffer systems are those that are physiologically compatible with the patient and can maintain a pH value in the range of about 3.5 to about 7, preferably about 4 to about 7, e.g., an acetic acid/sodium acetate buffer, a citric acid/sodium citrate buffer, and the like.

Pharmaceutically acceptable excipients that can be included in the pharmaceutical gel compositions of the present invention include, for example, physiologically tolerable surfactants, solvents, emollients, colorants, fragrances, and the like, which are well known in the art. The compositions preferably have a pH value in the range of about 3.5 to about 7. Other preferred embodiments have a pH value in the range of about 4 to about 7.

A preferred embodiment of the pharmaceutical gel composition of the present invention comprises, on a total composition weight basis, about 0.1 to about 3 weight percent of benzydamine hydrochloride and about 16 to about 35 weight percent of a poloxamer polymer in water preferably having a pH in the range of about 3.5 to about 7. The weight ratio of water to poloxamer in the composition is preferably less than about 4:1, more preferably not more than about 3:1. The composition also contains about 2 to about 50 weight percent of propylene glycol, more preferably about 3 to about 30 weight percent.

A particularly preferred pharmaceutical gel composition of the present invention comprises, on a total composition weight basis, about 0.75 to about 2 weight percent of benzydamine hydrochloride, about 16 to about 35 weight percent of a poloxamer polymer, up to about 25 weight percent of glycerin, and about 2 to about 30 weight percent of propylene glycol, in water preferably having a pH in the range of about 3.5 to about 7. The weight ratio of water to poloxamer polymer in the composition more preferably is not more than about 3:1.

A method of treating vaginal infections according to the present invention comprises the steps of contacting the vagina of a patient suffering from a vaginal infection, such as a bacterial or yeast infection, with a therapeutically effective amount of a pharmaceutical gel composition of the present invention. Preferably the pharmaceutical gel composition comprises, on a total composition weight basis, about 0.1 to about 3 weight percent of benzydamine hydrochloride, about 16 to about 35 weight percent of a polyoxyalkylene block copolymer in water preferably having a pH value in the range of about 3.5 to about 7. The composition also includes about 2 to about 50 weight percent of propylene glycol and up to about 25 weight percent of glycerin. The weight ratio of water to polyoxyalkylene polymer in the composition preferably is less than about 4:1, more preferably is not more than about 3:1.

A presently preferred technique for contacting the vagina with a gelled pharmaceutical composition of the present invention is to extrude the gelled composition through a tubular applicator from a storage vessel, such as a syringe, squeezable tube, or the like, into the patient's vagina. The volume of gelled composition so contained within such vessel is conveniently and preferably selected so as to constitute a single dose, or two or more doses, so as to facilitate administration of a desired controlled dose to the patient's vagina. The storage vessel is initially sealed, but is opened at the time of use. If more than a single dose is present, the vessel is preferably resealable by a suitable closure means. Another presently preferred method of application is a pre-filled single unit-dose vaginal applicator that can be disposed of after the unit dose is dispensed therefrom.

Another presently preferred technique is to employ a single use packet (such as a small envelope-like structure, or the like) containing an intended single unit dose. The packet is initially sealed, but is opened at the time of use by tearing, cutting, or the like at a desired or planned location in the packet after which the packet is manually squeezed so that the contents are directly administrable as desired Generally, the dosage of the composition to be contacted with the patient's vagina can vary with the age, condition, and type of infection suffered by the patient, and can be determined by one of skill in the art. The dosage can also be adjusted by the individual physician in the event of any complication.

The quantity of benzydamine hydrochloride contained in a unit dose is generally at least about 5 milligrams (mg), and preferably is not more than about 100 mg. A typical and presently more preferred unit dose in a gel vehicle is in the range of about 20 to about 50 mg per dose.

Such a quantity can be administered 1 to 2 times daily (i.e., at spaced intervals during a 24-hour period) in a single day, or over a period of up to about 7 days. A typical daily dose thus delivered can range from about 20 to about 100 mg. The usual total dose during the course of therapy for the gelled pharmaceutical compositions of the present invention is in the range of about 60 mg to about 500 mg. A presently preferred administration procedure is to employ a unit dose of about 5 grams of the gel (delivering a dose of about 25 mg of benzydamine hydrochloride) administered once or twice daily for a period of about 3 days, thereby to deliver a total dose in the range of about 75 mg to about 150 mg. Those skilled in the art will appreciate that the foregoing dose levels are provided illustratively, and that higher and lower dose levels can be employed without departing from the spirit and scope of the present invention.

Preferably, the composition remains in contact with the patient's vagina for a period of time sufficient for substantially all of the active agent (i.e., benzydamine) to be gradually released from the gel. The gelled composition preferably remains in contact with the patient's vagina for a period of time in the range of about 12 to about 36 hours.

Another aspect of the present invention is an article of manufacture comprising packaging material and a gelled pharmaceutical composition of the invention within the packaging material. The gelled pharmaceutical composition is present in an amount sufficient to treat a vaginal infection in a patient, preferably in an amount equivalent to at least one unit dose. The packaging material comprises a label that indicates that the gelled pharmaceutical composition can be used for treating vaginal infections. Preferably the label includes other printed indicia such as a listing of ingredients, the manufacturer's name and address, and the like. Preferably the packaging material also includes a printed insert including detailed information on the composition, its method of administration for treatment of vaginal infections, side effects, contraindications, and the like indicia, which may be required by governmental agencies responsible for regulation of pharmaceutical products.

The following non-limiting examples further illustrate the present invention.

EXAMPLE 1

Preparation of a Gelled Benzydamine Hydrochloride Gel A of the Present Invention Chilled water was buffered to a pH value of approximately 4.25 by the addition of sodium acetate and acetic acid. About 24 parts by weight poloxamer 407 (Pluronic F127 from BASF Corp.) was dispersed in about 58 parts by weight of buffered water. About 0.05 parts by weight EDTA was then added. About 0.08 parts by weight of methyl paraben and about 0.02 parts by weight propyl paraben was dissolved in about 3 parts by weight propylene glycol and added to the water/poloxamer solution. Benzydamine hydrochloride (about 2 parts by weight) was dissolved in water (about 15 parts by weight). The benzydamine solution was then added to the water/poloxamer solution. Additional water was added to bring the composition to 100 parts by weight. This entire process was performed in an ice bath to keep the composition at about 5° C., at which temperature it is a clear liquid. The composition was stored overnight in a refrigerator at about 5° C. The following morning the composition was removed from the refrigerator and allowed to warm slowly to room temperature. At room temperature the composition was a clear, viscous gel.

EXAMPLE 2

Preparation of Benzydamine Hydrochloride Gels B–N of the Present Invention

Benzydamine hydrochloride Gels B–N were prepared following the general procedure of Example 1. The pH and amounts of each of the components in the compositions are provided in Table 1, in percent by weight (pbw).

TABLE 1

Pharmaceutical Gel Compositions

| Gel | pH | B-HCl (pbw) | F127 (pbw) | PG (pbw) | Other Components (pbw) |
| --- | --- | --- | --- | --- | --- |
| A | 4.37 | 2 | 24 | 3 | parabens, EDTA* |
| B | 5.51 | 2 | 24 | 3 | parabens, EDTA* |
| C | 6.18 | 2 | 24 | 3 | parabens, EDTA* |
| D | na | 2 | 20 | 18 | ** |
| E | na | 2 | 25 | 0 | ** |
| F | na | 2 | 30 | 0 | ** |
| G | na | 2 | 16 | 10 | glycerin (10)** |
| H | 4.49 | 0.5 | 24 | 3 | parabens, EDTA* |
| I | 4.43 | 1 | 24 | 3 | parabens, EDTA* |
| J | 6.03 | 2 | 24 | 3 | glycerin (27), parabens, EDTA* |
| K | 6.65 | 0.5 | 24 | 3 | parabens, EDTA* |
| L | 6.53 | 1 | 17 | 30 | parabens, EDTA* |
| M | 6.24 | 2 | 17 | 30 | parabens, EDTA* |
| N | 5.85 | 1 | 15 | 2.4 | glycerin (24), parabens, EDTA* |

*0.05 percent by weight EDTA, 0.02 percent by weight methyl paraben, 0.08 percent by weight propyl paraben, and a quantity of water sufficient to make up 100 percent by weight.
**a quantity of water sufficient to make up 100 percent by weight); na = not available.

In Table 1, "pbw" refers to percent by weight; "F127" refers to PLURONIC® F127 poloxamer polymer; and "PG" is propylene glycol. The pH values of Gels A, B, H and I were adjusted to the indicated value by addition of a sufficient quantity of acetic acid/sodium acetate buffer.

EXAMPLE 3

Evaluation of Antibacterial and Antifungal Activity of Gels A–J of the Present Invention About 1 gram of each Gel was deposited on an agar plate that was previously inoculated with *Staphylococcus aureus*

(ATCC 6538), a Gram-positive bacterium, and the plates were incubated for about 20 to about 28 hours at a temperature of about 35 to about 39° C. Antibacterial activity was evaluated by measuring the diameter of the zone of inhibition (i.e., a clear zone with no bacterial colonies present, measured in millimeters) around the deposited gel.

Similar plates were prepared wherein the inoculant was Candida albicans (ATCC 10231) and the plates were incubated about 24 to about 48 hours at about 23 to about 27° C. Antifungal activity was evaluated by measuring the diameter of the zone of inhibition (i.e., a clear zone, measured in millimeters, with no observed C. albicans growth) around the deposited gel.

A commercially available vaginal cream formulation of benzydamine hydrochloride, TANTUM ROSA® cream, available from Angelini Pharmaceuticals, Rome, Italy was also evaluated, for comparison. According to the manufacturer's product literature TANTUM ROSA® cream contains about 0.5% benzydamine hydrochloride in a cream base containing propylene glycol, saturated triglycerides, ceteth 20, hydroxyethyl cellulose, sodium citrate dihydrate, citric acid monohydrate, benzoic acid, and purified water. In addition, a simple aqueous solution containing 0.5% by weight of benzydamine hydrochloride in deionized water was tested as a positive control. All materials were tested in triplicate.

The results of the inhibition tests are provided in Table 2. As is apparent from the data in Table 2, the benzydamine-containing gels of the present invention are active against both the bacterium and yeast species, as was the aqueous solution of benzydamine hydrochloride. The commercial cream was not effective against either S. aureus or C. albicans under these test conditions. These results indicate that the gels of the present invention provide a treatment for vaginal infections that is superior to the commercial benzydamine cream product, and in an aqueous gel form suitable for adhesion to vaginal tissue for prolonged exposure to the active agent.

TABLE 2

Bacterial and Yeast Inhibition

| Composition | C. albicans clear zone, mm | S. aureus clear zone, mm |
|---|---|---|
| TANTUM ROSA ® | 0 | 0 |
| B-HCl in water | 12 | 14 |
| Gel A | 33 | 32 |
| Gel B | 34 | 33 |
| Gel C | 33 | 33 |
| Gel D | + | + |
| Gel E | + | 19 |
| Gel F | + | 17 |
| Gel G | 18 | 9 |
| Gel H | 0 | 0 |
| Gel I | na | na |
| Gel J | 35 | 33 |

+ means a zone of inhibition was observed but the size was not measured due to formulation sliding on the plate;
na = not available.

EXAMPLE 4

Evaluation of Benzydamine Release Rates from Gels of the Present Invention into a Saline Medium About 0.18 grams of Gel A from Example 1 was placed in a section (about 6 cm) of cellulose dialysis tubing having a molecular weight cut-off of about 12,000 Daltons (average flat width of about 9 mm, Sigma Chemical Company, St. Louis, Mo.) and the ends of the tubing were sealed with plastic clips. The sealed tube was suspended horizontally in a petri dish containing about 50 mL of 0.9% by weight aqueous sodium chloride solution (i.e., physiological saline medium). The saline medium was continually stirred and the amount of released benzydamine hydrochloride in the medium was periodically determined by measuring the UV absorbance of the medium at a wavelength of about 308 nm with a spectrophotometer and comparing the measured absorbance with an appropriate calibration curve, as is well known in the art. The medium was replaced with fresh saline medium after each determination of released benzydamine hydrochloride to prevent equilibration and maintain a sink for the benzydamine hydrochloride. Determinations of released benzydamine hydrochloride were performed about 1.5 hours, 3 hours, 5 hours, 8 hours, 12 hours, and 24 hours after initial emersion of the dialysis tubing containing the gel in the saline medium.

This procedure was repeated with Gels D, H, I and N (about 0.2 grams of gel), as well as for TANTUM ROSA® cream (about 0.12 grams). The release data are provided in Table 3. Numerical data in the table is rounded to the nearest 1%. Percent-released values greater than 100% indicate an experimental error of measurement in the range of about 3–4% for the UV detection method.

TABLE 3

Benzydamine Release Rate in Saline.

| Composition | 1.5 hr | 3 hr | 5 hr | 8 hr | 12 hr | 24 hr |
|---|---|---|---|---|---|---|
| Gel A | 24% | 42% | 62% | 77% | 89% | 98% |
| Gel D | 23% | 41% | 61% | 75% | 86% | 95% |
| Gel H | 21% | 36% | 55% | 71% | 85% | 103% |
| Gel I | 20% | 36% | 52% | 66% | 80% | 96% |
| Gel N | 29% | 51% | 73% | 88% | 97% | 104% |
| TANTUM ROSA ® | 69% | — | 102%* | 102% | 102% | 102% |

*data point taken at 4 hours instead of 5.

The data in Table 3 indicate that the gelled pharmaceutical compositions of the present invention provide a relatively sustained release of benzydamine hydrochloride into a saline medium in comparison with a commercial benzydamine hydrochloride cream formulation, which releases the total content within about 4 hours.

The pharmaceutical gels of the present invention provide a convenient and effective treatment for vaginal infections due to bacteria and yeast. The gel formulation affords a mucoadhesive vehicle for delivery of benzydamine hydrochloride, which can remain in contact with vaginal tissue for a prolonged period of time. The pharmaceutical gels of the present invention also provide a sustained release dosage form of benzydamine hydrochloride that is effective against both bacteria and yeast.

The foregoing specification enables one skilled in the art to practice the invention. Indeed, various modifications of the invention in addition to those shown and described herein will become apparent to those skilled in the art from the foregoing description and fall within the scope of the appended claims.

We claim:

1. A pharmaceutical composition having a gel consistency at room temperature and comprising, on a total composition weight basis, about 0.1 to about 3 weight percent of benzydamine hydrochloride, about 16 to about 35 weight percent of a polyoxyethylene/polyoxypropylene block copolymer, and about 2 to about 30 weight percent of propylene glycol, in water having a pH in the range of about 3.5 to about 7; wherein the polyoxyethylene/polyoxypropylene block copolymer comprises the gelling agent, and the weight ratio of water to block copolymer in the composition is less than about 4:1.

2. The composition in accordance with claim 1 wherein the benzydamine hydrochloride is present in the composition in an amount in the range of about 0.75 to about 2 weight percent on a total composition weight basis.

3. The composition in accordance with claim 1 wherein the polyoxyethylene/polyoxypropylene block copolymer has the general formula:

$$HO(CH_2CH_2O)_x(CH(CH_3)CH_2O)_y(CH_2CH_2O)_zH,$$

wherein x, y, and z are each independently numbers in the range of about 10 to about 150.

4. The composition in accordance with claim 3 wherein x and z are substantially equal to one another.

5. The composition in accordance with claim 3 wherein x and z are each in the range of about 98 to about 101, and y is in the range of about 56 to about 67.

6. The composition in accordance with claim 1 further comprising glycerin.

7. The composition in accordance with claim 6 wherein the glycerin is present in the composition in an amount in the range of up to about 25 weight percent on a total composition weight basis.

8. The composition in accordance with claim 1 further comprising at least one physiologically tolerable preservative agent.

9. The composition in accordance with claim 8 wherein the preservative agent is a paraben, a chelating agent, or a mixture thereof.

10. The composition in accordance with claim 9 wherein is methyl paraben, propyl paraben, or a mixture thereof.

11. The composition in accordance with claim 9 wherein the chelating agent is EDTA or a salt thereof.

12. The composition in accordance with claim 1 wherein the composition has a pH value in the range of about 4.0 to about 7.

13. The composition in accordance with claim 1 further comprising a buffer system.

14. The composition in accordance with claim 1 wherein the weight ratio of water to block copolymer in the composition is not more than about 3:1.

15. A pharmaceutical composition having a gel consistency that comprises, on a total composition weight basis, about 0.75 to about 2 weight percent of benzydamine hydrochloride, about 16 to about 35 weight percent of a polyoxyethylene polyoxypropylene block copolymer, up to about 25 weight percent of glycerin, and about 2 to about 30 weight percent of propylene glycol, in water having a pH in the range of about 3.5 to about 7, wherein the block copolymer comprises the gelling agent, and the weight ratio of water to block copolymer in the composition is not more than about 3:1.

16. An article of manufacture comprising packaging material and a pharmaceutical composition having a gel consistency within the packaging material; the pharmaceutical composition being present in an amount sufficient to treat a vaginal infection in a patient; the packaging material comprising a label that indicates that the pharmaceutical composition can be used for treating a vaginal infection; and the composition comprising, on a total composition weight basis, about 0.1 to about 3 weight percent of benzydamine hydrochloride, about 16 to about 35 weight percent of a polyoxyethylene/polyoxypropylene block copolymer, and about 2 to about 30 weight percent of propylene glycol, in water having a pH value in the range of about 3.5 to about 7, wherein the block copolymer comprises the gelling agent, and the weight ratio of water to block copolymer in the composition is less than about 4:1.

17. The article of manufacture in accordance with claim 16 wherein the packaging material further includes an insert comprising printed indicia selected from the group consisting of a description of the ingredients in the composition, the method of administration of the composition for treatment of vaginal infections, the side affects of the composition, contraindications to the use of the composition, and combinations thereof.

18. The article of manufacture in accordance with claim 16 wherein the gelled pharmaceutical composition further comprises up to about 25 weight percent of glycerin, on a total composition weight basis.

19. The article of manufacture in accordance with claim 16 wherein the benzydamine hydrochloride is present in the composition in an amount in the range of about 0.75 to about 2 weight percent, on a total composition weight basis.

20. The article of manufacture in accordance with claim 16 wherein the weight ratio of water to block copolymer in the composition not more than about 3:1.

21. The article of manufacture in accordance with claim 16 wherein the pharmaceutical composition comprises 0.75 to about 2 weight percent of benzydamine hydrochloride, about 16 to about 35 weight percent of a polyoxyethylene/polyoxypropylene block copolymer, and about 2 to about 30 weight percent of propylene glycol, in water having a pH in the range of about 3.5 to about 7, wherein the weight ratio of water to block copolymer in the composition is not more than about 3:1.

* * * * *